US009760337B2

United States Patent
Demharter (10) Patent No.: US 9,760,337 B2
(45) Date of Patent: Sep. 12, 2017

(54) GENERATING A SIGNAL (71) Applicant: Nikolaus Demharter, Dormitz (DE)

(72) Inventor: Nikolaus Demharter, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 680 days.

(21) Appl. No.: 14/272,879

(22) Filed: May 8, 2014

(65) Prior Publication Data
US 2014/0337397 A1   Nov. 13, 2014

(30) Foreign Application Priority Data

May 8, 2013 (DE) .......... 10 2013 208 519

(51) Int. Cl.
*G06F 5/01* (2006.01)
*G01R 33/36* (2006.01)
*A61B 5/055* (2006.01)

(52) U.S. Cl.
CPC .......... *G06F 5/01* (2013.01); *G01R 33/3607* (2013.01); *A61B 5/055* (2013.01)

(58) Field of Classification Search
CPC ..... G01R 33/20; G01R 33/32–33/3692; G01R 33/44; G01R 33/48; G01R 33/54–33/543
See application file for complete search history.

(56) References Cited

U.S. PATENT DOCUMENTS

| 5,140,268 A * | 8/1992 | Chan ................. G01R 33/3614 324/307 |
| 5,442,292 A | 8/1995 | Kolem et al. |
| 2007/0222449 A1* | 9/2007 | Hoult ................. G01R 33/583 324/318 |
| 2012/0224647 A1 | 9/2012 | Huber et al. |
| 2014/0266190 A1* | 9/2014 | Bollenbeck ........ G01R 33/3692 324/307 |

FOREIGN PATENT DOCUMENTS

DE     102010035918 A1     3/2012

OTHER PUBLICATIONS

German Office Action for German Application No. 10 2013 208 519.2, mailed Apr. 2, 2014, with English Translation.

* cited by examiner

*Primary Examiner* — Matthew Sandifer
(74) *Attorney, Agent, or Firm* — Lempia Summerfield Katz LLC (57) ABSTRACT

A method for generating a signal for a transmission antenna in a magnetic resonance imaging system includes generating a real part and an imaginary part of a baseband signal, generating a real part and an imaginary part of variations in frequency and in phase, and performing a complex multiplication of the baseband signal with the variations in frequency and in phase and a radiofrequency carrier signal for modulation. The method also includes modifying the modulated signal, and may include establishing a characteristic angle for a phase shift of the modified signal, and correcting the modulation based on the established angle in a closed-loop control.

18 Claims, 10 Drawing Sheets

GENERATING A SIGNAL

This application claims the benefit of DE 10 2013 208 519.2, filed on May 8, 2013, which is hereby incorporated by reference in its entirety.

BACKGROUND

The present embodiments relate to generating a signal for a transmission antenna in a magnetic resonance imaging system.

Using magnetic resonance imaging (MRI), slice images of the human or animal body may be generated. The slice images permit an assessment of the organs and many pathological organ changes. MRI is based upon very strong magnetic fields generated in a magnetic resonance imaging (MRI) system and alternating magnetic fields in the radiofrequency range, by which specific atomic nuclei (e.g., the hydrogen nuclei/protons) are resonantly excited in the body. As a result of this, an electric signal is induced in a receiver circuit.

MRI systems may have a transmitter that is provided to generate a substantially homogeneous radiofrequency field for exciting the nuclear spins. The associated transmitter antenna, which is also referred to as "body coil", may be fixedly installed in the magnet and the gradient coils. As an example, a "birdcage" antenna includes a cylindrical form and substantially consists of two rings that are connected to one another using a number of uniformly spaced apart antenna rods arranged in parallel. Connection points of the antenna rods on the rings are connected to one another via a capacitor. The capacities of the capacitors are selected such that the antenna arrangement is resonant at the examination frequency (e.g., between 60 and 125 MHz).

For the spatial resolution of the signals, the frequency and phase encoding is imaged in the pulse sequences transmitted by the transmission antenna. Therefore, a corresponding module for generating variations in frequency and in phase is provided in a corresponding signal generation module arranged upstream of the transmission antenna. The module for generating variations in frequency and in phase actuates a digitally controlled oscillator and generates the corresponding vibrations. The baseband data generated in a baseband module are modulated by the variations in frequency and in phase and the radiofrequency carrier signal. This may take place in complex number space (e.g., the individual signals are produced as real and imaginary parts and modulated by multiplication).

The generated modulated signal, which may be a single-sideband modulation (SSB) signal, is transmitted to an amplifier (e.g., radiofrequency power amplifier, RFPA). The RFPA amplifies the signal and transfers the signal to the transmission antenna. For linearization purposes, a control loop may be embodied with the aid of a directional coupler (DICO) and a coherent demodulation. This control loop acts on the generated baseband data and may correct not only the amplitude, but also the phase of the SSB signal.

Depending on the adaptation of the transmission antenna, the power is reflected back into the RFPA. The RFPA is to be configured for this reflected power since there is a superposition of the forward-directed wave and the reflected wave. Alternatively or additionally, with the aid of a circulator, the reflected power may be directed to a load instead of into the RFPA. A circulator is a component that routes the power in a circular manner from one port to the next. As a result, the reflected power is no longer fed back to the RFPA, but rather into a load.

The nonlinearities created by the circulator may likewise be corrected in this case (e.g., by the temporal properties thereof or the properties that change with the temperature). This is because a circulator changes properties during the operation in a manner characterized by the scattering parameters. It is therefore desirable for the control loop to also register the nonlinear and time-changing properties (e.g., depending on other variables such as temperature) of the circulator (e.g., for the circulator to be part of the control loop).

SUMMARY AND DESCRIPTION

The scope of the present invention is defined solely by the appended claims and is not affected to any degree by the statements within this summary.

The closed-loop control of the prior art becomes unstable in the aforementioned control loop if the circulator is included. As a result, the signal generation module may not be operated without further complicated technical adaptations.

The present embodiments may obviate one or more of the drawbacks or limitations in the related art. For example, a method for generating a signal for a transmission antenna in a magnetic resonance imaging system that enables reliable signal generation without being too technically complex is provided.

According to one or more of the present embodiments, the method includes establishing a characteristic angle for a phase shift of the modified signal, and correcting the modulation based on the established angle in the style of closed-loop control.

The instability in the closed-loop control is caused by the high variation in the phase as a result of the circulator. Indeed, measurements have shown that a significant variation in the phase is generated by the circulator. The variation is also load-dependent. By contrast, the closed-loop control only has a restricted operating range with respect to the maximum phase deviation. A phase actuator or phase-shifter may be situated directly on the input or output of the circulator. This would, however, once again need a separate control loop (e.g., by continuously determining the phase difference between input and output of the circulator). The phases would be measured again by separate directional couplers. However, this provides a significant increase in the technical complexity. A reduction in the additional complexity would be possible by replacing the continuous measurement of the phase difference by a temperature measurement of the circulator. This is because the phase variation as a result of the circulator depends substantially on the temperature thereof, and actuation of the phase-shifter derived therefrom would be possible. Although this may not compensate the phase change in the circulator as well as a direct measurement, a substantial reduction may be provided. In this case too, the additional complexity in terms of the required hardware is still significant.

In order to realize a more stable closed-loop control without significant additional hardware complexity, the goal is therefore to extend the closed-loop control range for the phase without adversely affecting the dynamic properties of the RF closed-loop control. The variables to be corrected by the RF closed-loop control are very fast, where the phase response caused by the circulator is orders of magnitude slower. Therefore, the drift by the circulator may be corrected separately. An angle characteristic of the phase shift of the modified signal is initially established. By way of example, this may be brought about by an arctangent element. The phase angle established thus is then used to correct the modulation based on the established angle in the style of closed-loop control. This may be brought about by converting the correction angle into real and imaginary parts and a subsequent complex multiplication (e.g., with the baseband signal such that the drift generated by the circulator is compensated for).

Advantageously, the correction includes an addition to an output signal of a phase accumulator that is used in the generation of real and imaginary part of the variations in frequency and in phase. Such a phase accumulator is used in the direct digital synthesis of the variations in frequency and in phase and cyclically adds, every clock step, the input value added on the left-hand side, which inversely proportionally sets the frequency. The current counter value then corresponds to a phase angle, and an overflow of the phase accumulator (e.g., automatic jump back to zero) in this case corresponds to a full circulation of the phasor. By adding the correction phase angle to the output signal of the phase accumulator, this allows the phase correction to be taken into account in a particularly simple manner since the conversion and complex multiplication of the output signals of the phase accumulator of the variations in frequency and in phase, present in any case, are used as well.

In a further advantageous configuration, the difference between the phase angle of the demodulated modified signal and the phase angle of the baseband signal is used when establishing the characteristic angle. In other words, use is made of two arctangent elements. Real and imaginary parts of the demodulated signal are fed to one of the elements from the directional coupler of the closed-loop control. Real and imaginary parts of the baseband data are fed to the other element. Thus, the phase angle is established separately before and after the circulator. The phase angles of the elements are subtracted, and the phase difference is added, as described, to the variations in frequency and in phase.

In an alternative embodiment, the phase angle of a manipulated variable of the closed-loop control is used when establishing the characteristic angle. This is because, for systemic reasons, the RF closed-loop control already establishes the difference of baseband signal and output signal of the circulator, albeit in the Cartesian space (e.g., by subtraction of real and imaginary parts). Therefore, in this case, the phase angle of the difference may only be established with one arctangent element and used for addition to the variations in frequency and in phase.

In an additional advantageous configuration, the difference between the phase angle of the manipulated variable and the phase angle of the baseband signal is used when establishing the characteristic angle. In other words: the actuation angle of the baseband data is subtracted from the phase difference established by the closed-loop control. As a result, time-variable actuation angles of the baseband data become possible, which would otherwise be interpreted as error angles and be corrected. When the actuation angle is put into relation with the correction angle of the Cartesian closed-loop control, actuations with any phase angle or variable actuation angle (as in the case of baseband modulation) may be provided.

The control systems are based on a parallel comparison of input and output signals. The output signals are to be demodulated again. The elements used hereby in one of the parallel signal paths such as, for example, a controller or other components such as demodulators have time retardation. Advantageously, this time retardation of elements of the closed-loop control is compensated for (e.g., by time retardation elements that are introduced in the respectively other signal path).

Advantageously, certain values are accumulated from the established correction angle using a second phase accumulator when correcting the variations in frequency and in phase. This lifts the restriction of the error angle transferable in the phase closed-loop control. As a result of the second phase accumulator, relatively large angle changes (even greater than pi) occurring over relatively long time periods are accumulated and corrected.

The values entered into the second phase accumulator may be lifted to the desired level using a linear amplifier (e.g., gain block). Alternatively, a multiple decision may be used (e.g., the values accumulated in the second phase accumulator are determined based on a table with assignments between angle intervals and values). This allows simple closed-loop control.

The angle is determined in the arctangent blocks by converting Cartesian coordinates of the real and imaginary values into polar coordinates (e.g., only the angle in this case). This may be brought about in different ways (e.g., using the CORDIC algorithm). In one embodiment, the characteristic angle is determined based on a table with assignments between real and imaginary part intervals and angles. As a result, the block works particularly fast.

As already explained previously, the described method enables the use of a circulator in the modification of the modulated signal. In the specific measurement procedure, signal pulses are emitted. The phase error is corrected as described above. No values are available for the second phase accumulator during a time period between two signal pulses of the signal since no angles may be determined as a result of a lack of signal amplitude. In these time periods, the input values for the second phase accumulator are therefore advantageously determined based on the temperature of the circulator. The precise adaptation of the temperature model in this case depends on the design and the cooling of the circulator.

In a further exemplary configuration, the residual established correction angle is fed to the second phase accumulator as input value at the end of a signal pulse. This may be brought about by an additional element (e.g., a block for phase prediction). This is because the phase error remaining at the pulse end is present as residual error at the end of the radiofrequency pulse. The residual error may not previously be corrected during the pulse. If this value is fed to the phase accumulator (e.g., multiplied by a factor), the phase accumulator instantly jumps to the value that the circulator caused as phase error. As a result, corrections may be quicker. Subsequently, the temperature module is once again used in the pulse pause. However, due to the pulse end, the phase jump is no longer effective in the pulse itself. The pulse is not interfered with by a phase jump.

A signal generation module for a magnetic resonance imaging system is advantageously embodied for generating signals using the method described above.

A magnetic resonance imaging system includes such a signal generation module.

The advantages of one or more of the present embodiments, respectively, include it being possible to dispense with expensive power hardware such as, for example, phase actuators or additional phase measuring devices as a result of transferring the angle error from the addition of the Cartesian closed-loop control to complex multiplication. RFPAs with integrated circulator and DICO may be used. The circuits used to solve the problem may be implemented within a field programmable gate array (FPGA) or an application-specific integrated circuit (ASIC) with relatively low cost outlay. Compared to the temperature compensation, this also produces better compensation of the error angle.

DETAILED DESCRIPTION

In all figures, the same parts have been provided with the same reference signs.

Figure 1:
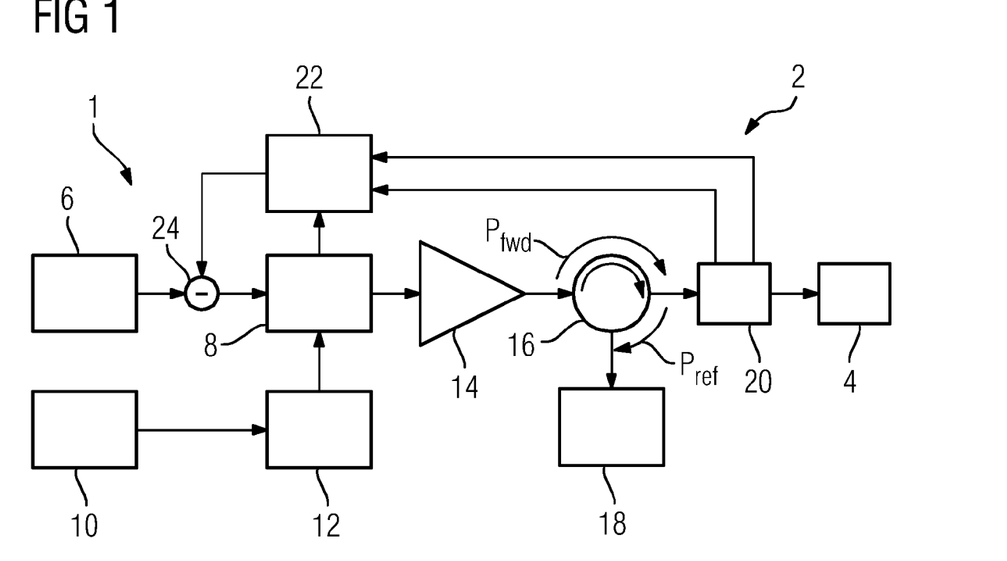
FIG. 1 shows part of one embodiment of a magnetic resonance imaging system with a signal generation module with circulator and control loop.

FIG. 1 shows one embodiment of a signal generation module 1 in a magnetic resonance imaging system 2, which is only depicted in sections. Apart from the signal generation module 1, all that is shown is a transmission antenna 4. Further parts, such as magnets, reception coils and the evaluation unit, are not shown in FIG. 1. The transmission antenna 4 is embodied as a "body coil". The principle of an MRI measurement is briefly explained in the following.

The actual measurement is brought about by a spin echo sequence. In this context, a "sequence" (e.g., a "pulse sequence") is a combination of radiofrequency pulses and magnetic gradient fields, with a specific frequency or strength, that are switched on and off in a predetermined sequence many times in each second. Initially, a radiofrequency pulse with the right frequency (e.g., Larmor frequency), the 90° excitation pulse, is present. As a result thereof, the magnetization is deflected by 90° across the external magnetic field. The magnetization starts to circle around the original axis (e.g., precession).

The radiofrequency signal generated in the process may be measured outside of the body. The radiofrequency signal reduces exponentially because the proton spins get out of "sync" (e.g., "dephase") and increasingly superpose in a destructive manner. The time after which 63% of the signal has decayed is referred to as relaxation time (e.g., spin-spin relaxation). This time depends on the chemical surroundings of hydrogen. This time is different for every tissue type. By way of example, tumor tissue may have a longer time than normal muscular tissue. This is why a weighted measurement depicts the tumor more brightly than surroundings of the tumor.

In order to be able to assign the measured signals to the individual volume elements (e.g., voxels), a spatial encoding is generated by linearly spatially dependent magnetic fields (e.g., gradient fields). What is employed here is that the Larmor frequency for a specific particle depends on the magnetic flux density (e.g., the strength of the field component perpendicular to the direction of the particle angular momentum increases with Larmor frequency). A gradient is applied during the excitation and provides that only a single slice of the body has a fitting Larmor frequency (e.g., only the spins in this slice are deflected (slice selection gradient)). A second gradient transverse to the first gradient is briefly switched on after the excitation and brings about controlled dephasing of the spins such that the precession of the spins in each image line has a different phase angle (e.g., phase encoding gradient). The third gradient is switched perpendicular to the other two gradients during the measurement. The third gradient provides that the spins in each image column have a different precession speed (e.g., transmit at a different Larmor frequency (read-out gradient, frequency encoding gradient)). Thus, all three gradients together bring about encoding of the signal in three spatial planes.

In FIG. 1, baseband data are generated in the baseband data block 6 and fed to a modulator 8. At the same time, the frequency/phase variations used for the above-described spatial resolution are determined in the frequency/phase variation block 10. The frequency/phase variation block 10 actuates a digitally controlled oscillator 12. The output signals of the digitally controlled oscillator 12 are likewise fed to the modulator 12. The modulator 12 carries out a modulation of the baseband data with the frequency/phase variations and the radiofrequency carrier signal. This is transmitted to an amplifier 14, designed as a RFPA. The RFPA amplifies the signal and emits the signal to the transmission antenna 4.

Depending on the adaptation of the transmission antenna 4, power is reflected back into the amplifier 14. With the aid of a circulator 16 arranged between the amplifier 14 and transmission antenna 4, the reflected power may be routed to a load 18 rather than into the amplifier 12. For linearization purposes, a control loop is formed with the aid of a directional coupler 20 that is arranged between the circulator 16 and transmission antenna 4, and a coherent demodulation in a demodulator 22. Using the directional coupler, the demodulator 22 registers the power transmitted in the direction of the transmission antenna 4 and demodulates the signal with the aid of input data from the modulator 8. The actual value established by the demodulator 22 is subtracted in a subtraction element 24, arranged between the baseband data block 6 and the modulator 8, from the baseband data signal.

Figure 2:
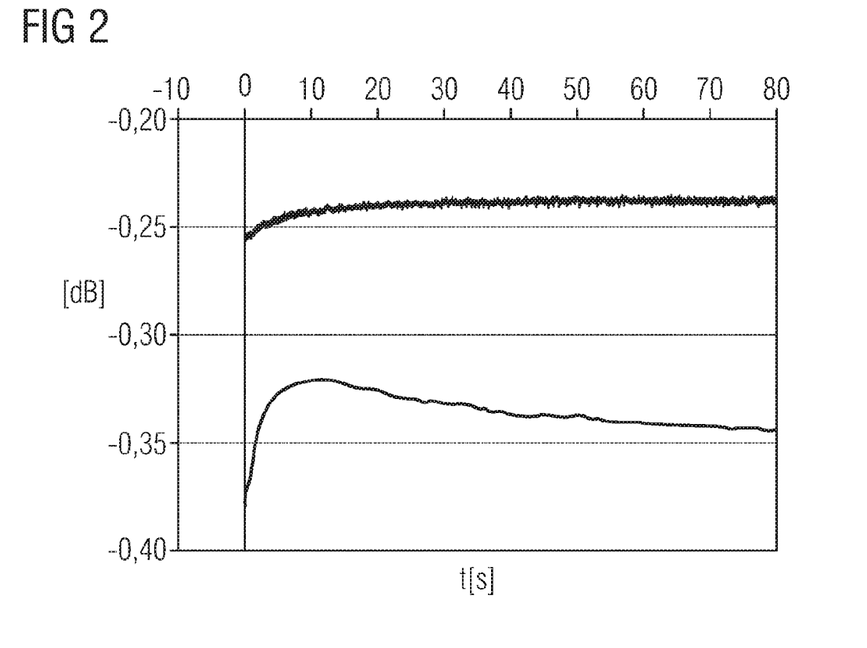
FIG. 2 shows a graph of exemplary insertion loss in decibel, plotted against the time in seconds, for a circulator at different transmission powers.
Figure 3:
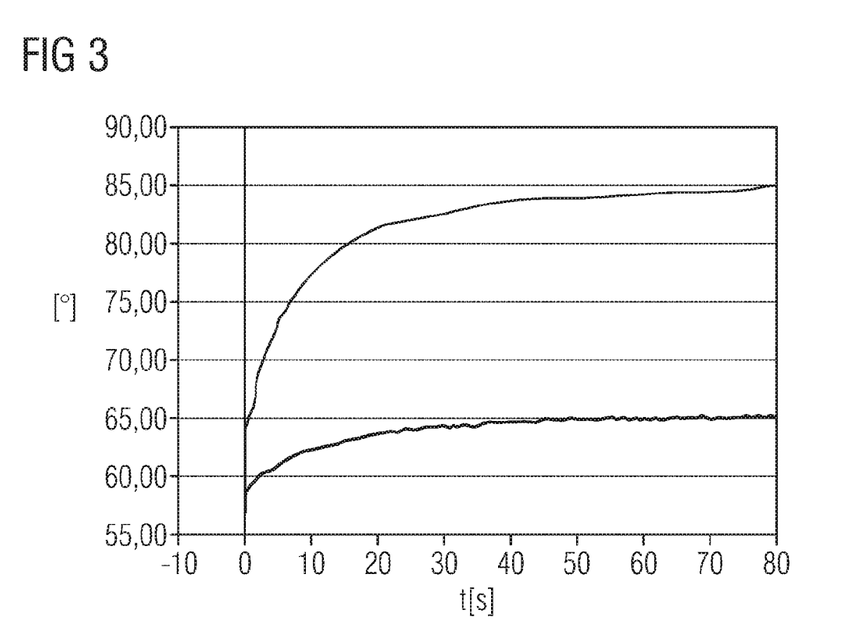
FIG. 3 shows a graph of exemplary phase shift in degrees, plotted against the time in seconds, for a circulator at different transmission powers.

FIG. 2 shows an exemplary insertion loss through the circulator 16 for a transmission power of 2.5 kW (upper curve) and 10 kW (lower curve), plotted in decibel (dB) against time in seconds (s). FIG. 3 shows the phase variation through the circulator 16 for a transmission power of 2.5 kW (lower curve) and 10 kW (upper curve), plotted in degrees against time in seconds (s). This results in damping from −0.23 to −0.35 dB and phase variations of up to 85 degrees. The variations are strongly load-dependent and may vary even more strongly. However, the closed-loop control shown in FIG. 1 only has a restricted operating range with respect to the maximum phase deviation and becomes unstable without additional measures in the case of such large phase deviations.

FIGS. 4 to 11 show different embodiments for the closed-loop control. What is shown in greater detail than in FIG. 1 in each case is the actuation part of the signal generation module 1. Amplifier 14, circulator 16, load 18, directional coupler 20 and transmission antenna 4 have been omitted. By way of example, the parts shown in FIGS. 4 to 11 may be realized on an FPGA or ASIC.

The baseband data block 6 generates a signal pair RE and IM (e.g., Cartesian real and imaginary values). These constitute the actuation signal. This actuation signal is still complemented by the actuation with respect to frequency and phase offset f and Φ, generated in the frequency/phase variation block 10. The oscillator 12 from FIG. 1 is depicted in more detail in FIGS. 4 to 11 and includes a phase accumulator 26. The output signal Φa thereof is converted into Cartesian coordinates in a converter 28.

Figure 4:
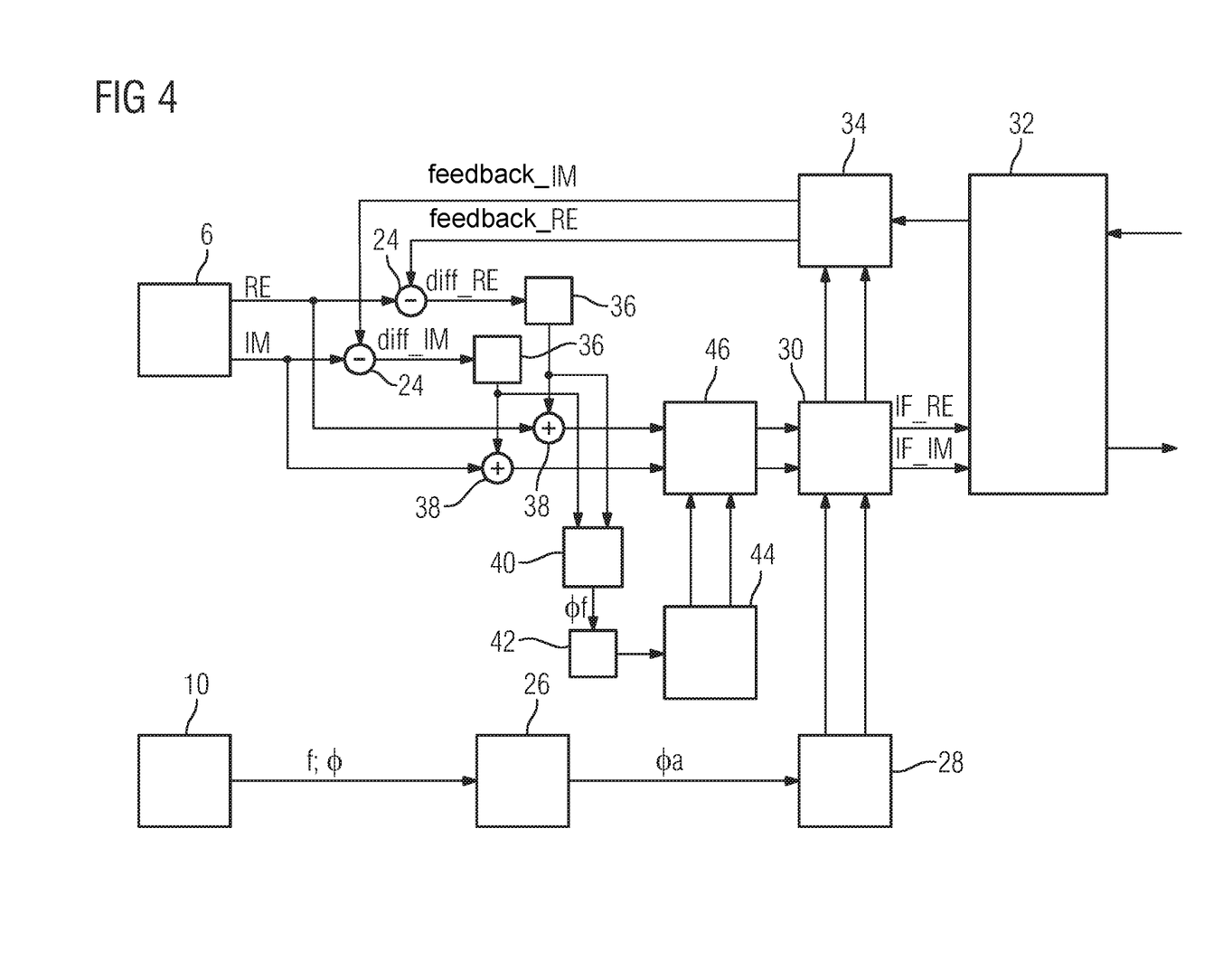
FIGS. 4 to 11 show parts, in sections, of different embodiments of the signal generation module with regulated phase correction.

The modulator 8 and the demodulator 22 are likewise depicted in more detail in FIG. 4. What is shown is a multiplication element 30 that performs complex multiplication on the signal pair RE and IM with the output signal Φa converted into Cartesian coordinates and therefore modulates this. The resultant signal pair IF_RE and IF_IM is routed through a function block 32 for further modulation and demodulation and is routed to the amplifier 14 as single sideband signal SSB.

The signal coming from the directional coupler 20 is likewise routed through the function block 32 and demodulated in a demodulation/filter block 34. As a result, the signal pair feedback_RE and feedback_IM is formed as an output value that constitutes the actual value signal. Thus, a phase change of the circulator 16 is reflected by this signal. The difference between the signal pair RE and IM and the signal pair feedback_RE and feedback_IM is formed in the subtraction elements 24. These difference signals diff_RE and diff_IM constitute the deviation of the intended signal from the actual signal and is fed into the PID controller 36, the output signal of which is added in addition elements 38 to the signal pair RE and IM routed to the multiplication element 30.

For stabilizing the closed-loop control, the output signal of the PID controllers 36 is additionally routed to an arctangent element 40. The arctangent element 40 extracts the phase information from the correction signal pair from the PID controllers in the form of a phase angle Φf. The phase angle Ff is attenuated in a damping/gain element 42 (gain), converted back into a Cartesian signal pair in a further converter 44 and is subjected to complex multiplication with the output signal of the addition elements 38 in the further multiplication element 46 arranged between multiplication element 30 and addition elements 38, before there is a further modulation. This complex multiplication brings about a correction of the phase within the meaning of a closed-loop control.

Figure 5:
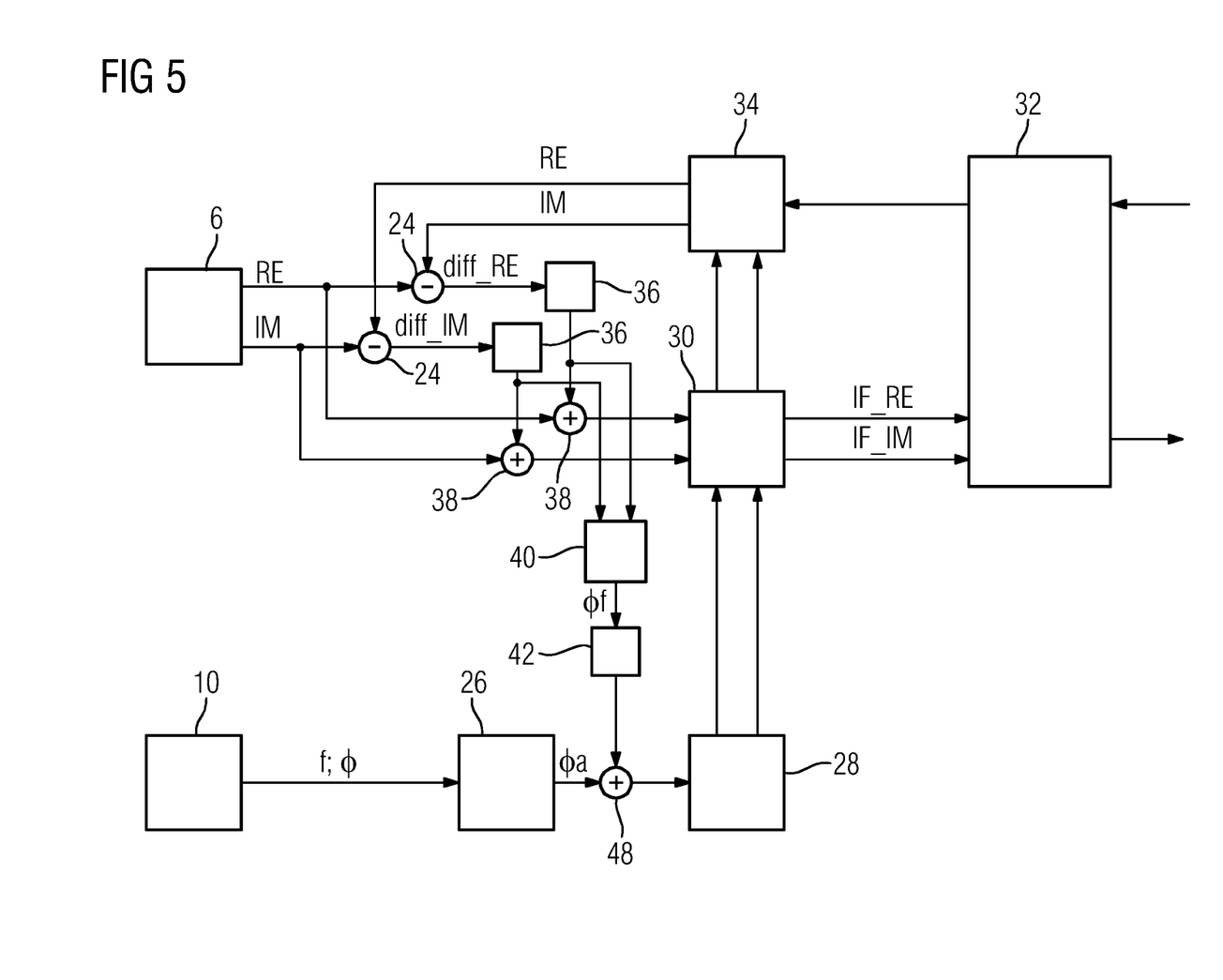

An alternative is shown in FIG. 5, which is only explained in terms of differences to FIG. 4. In FIG. 5, the separate converter 44 and multiplication element 46 are dispensed with. Instead, the output signal Φf of the arctangent element 40 and of the damping/gain element 42 is routed to an addition element 48 that is arranged between the phase accumulator 26 and the converter 28. The correction angle Φf is thus added directly to the actuation angle Φa, and the converter 28 and the multiplication element 30 are used for both angles.

Figure 6:
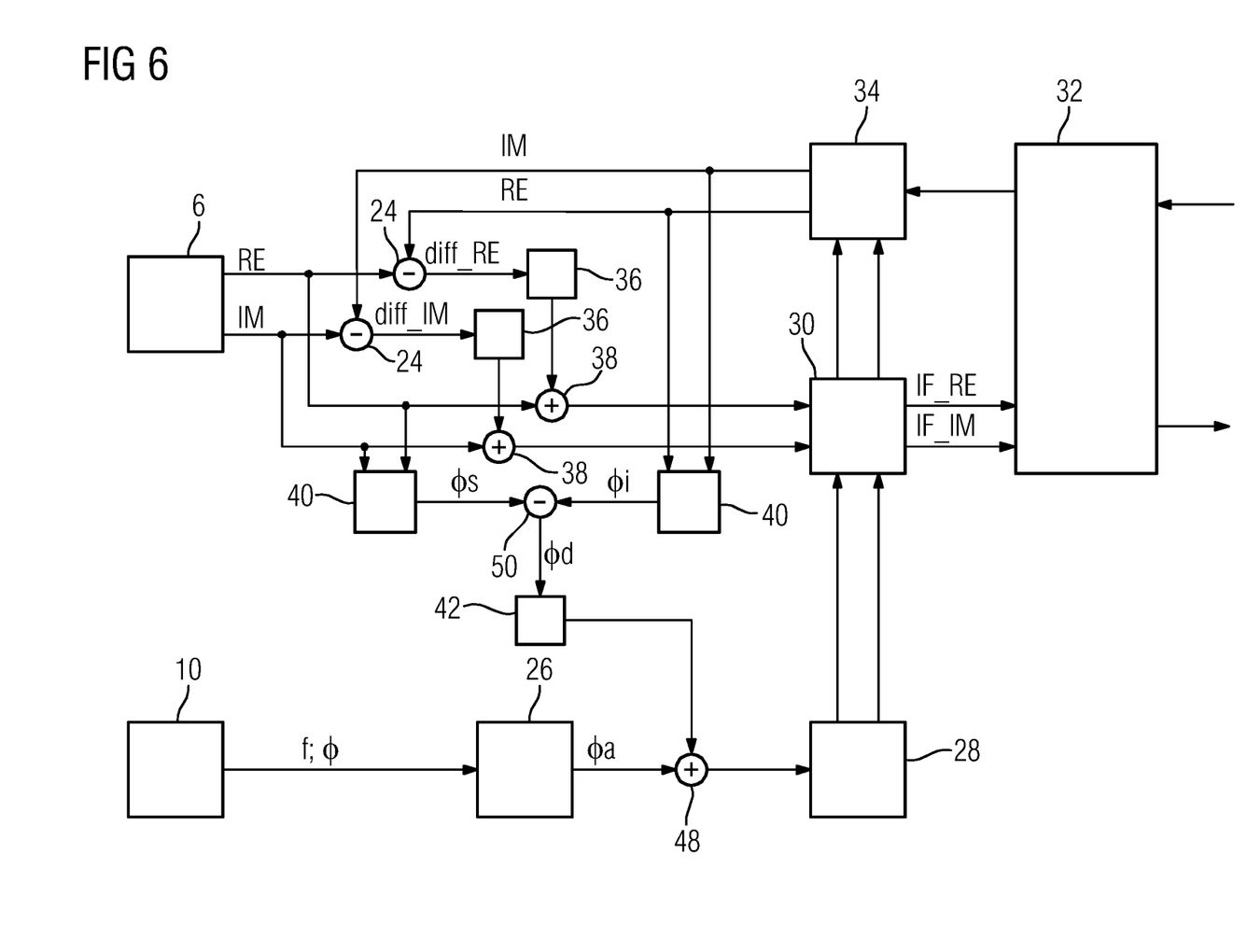

A further alternative is shown in FIG. 6, which is only explained based on differences to FIG. 5. Two arctangent elements 40 that extract the intended phase angle Φs from the Cartesian signal pair RE and IM, and extract the actual phase angle Φi from the Cartesian signal pair feedback_RE and feedback_IM are provided. The angles Φs and Φi are subtracted in a subtraction element 50, and the difference phase angle Φd is established thus. The difference phase angle Φd is routed to the damping/gain element 42 known from FIG. 5.

Figure 7:
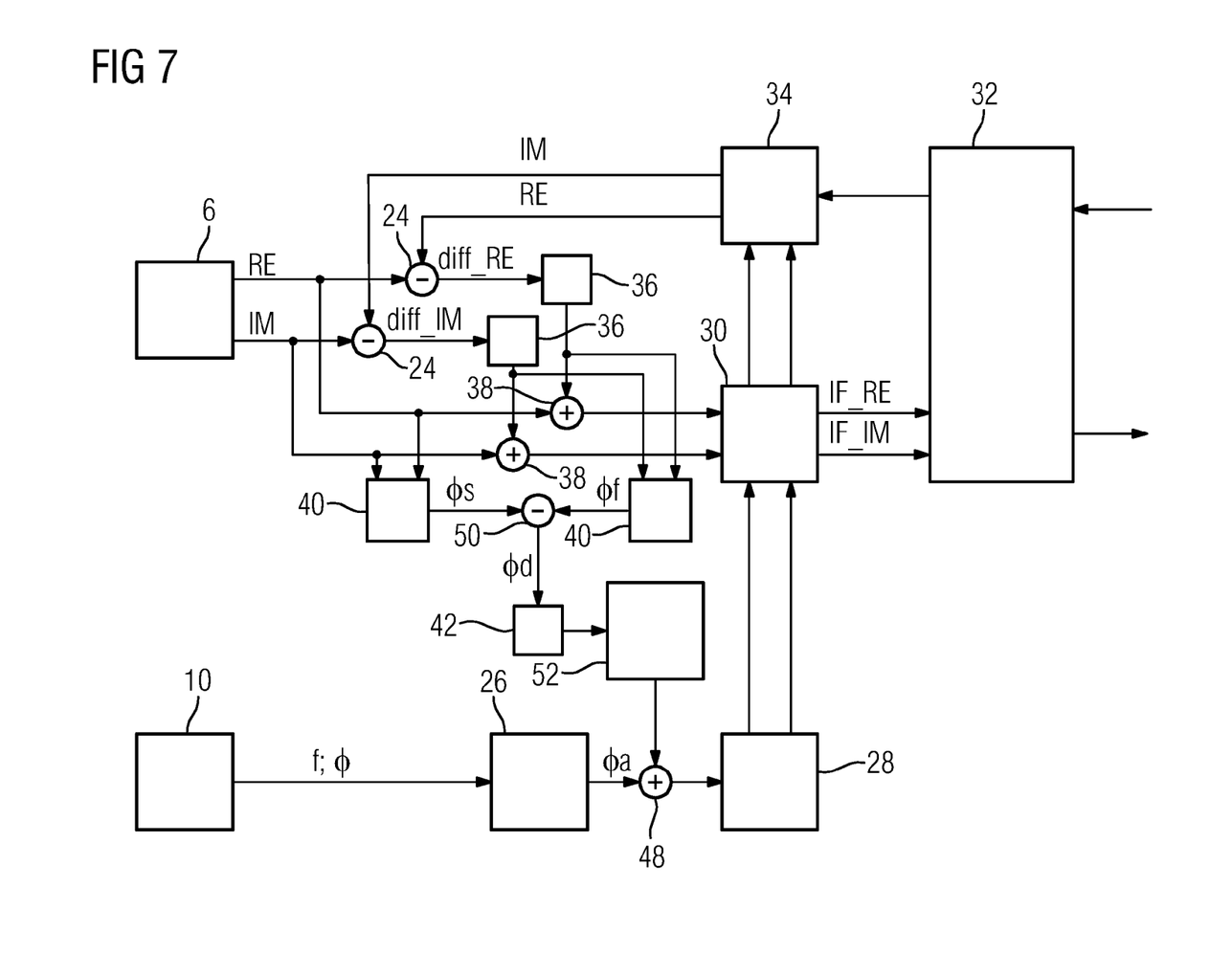

A further alternative is shown in FIG. 7, which is likewise only explained based on differences to FIG. 6. The two arctangent elements 40 establish the angle Φf from the output signals of the PID controllers 36 or the intended phase angle Φs, which corresponds to the current actuation angle. As a result, actuations at any phase angle may be provided. A further phase accumulator 52 is arranged between the damping/gain element 42 and the addition element 48. The phase accumulator accumulates large angle changes occurring over relatively long periods of time.

In the following FIGS. 8 to 10, multiplication element 30, converter 28, function block 32 and demodulation/filter block 34 have additionally been omitted for reasons of clarity. These correspond to the set-up from FIG. 7.

Figure 8:
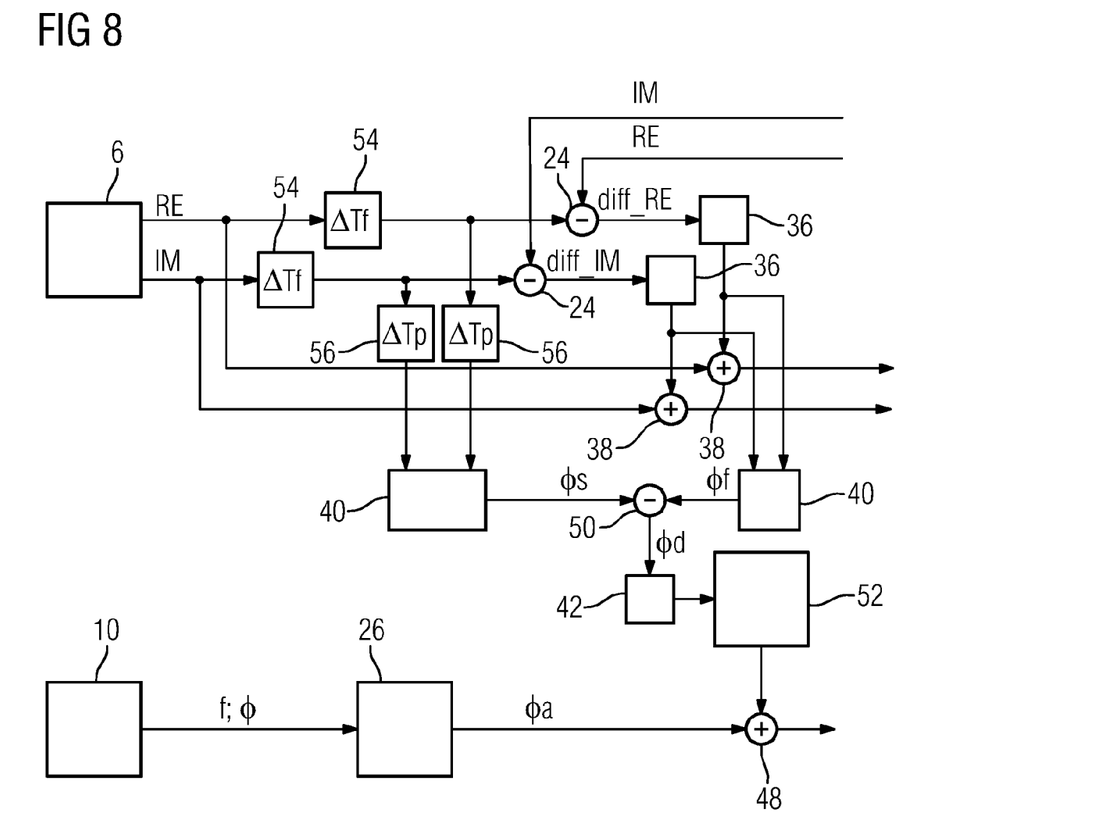

Otherwise, FIG. 8 is explained based on differences to FIG. 7. Retardation elements 54 are arranged between the subtraction elements 24 and the baseband data block 6. These correspond to the retardation of the whole control loop. Further retardation elements 56 are connected upstream of the arctangent element 40, which establishes the intended angle Φs. These correspond to the retardation from the PID controllers 36.

Instead of a linear damping/gain element 42, a decision may also be made based on a table that, for example, is illustrated in the following:

| Φf-Φs | Phase accumulator control | Comment |
| --- | --- | --- |
| −10° . . . +10° | 0 | No action, sole correction by Cartesian closed-loop control |
| +10° . . . +45° | 1 | Slow incrementing of phase accumulator |
| +45° . . . +90° | 2 | Medium-fast incrementing of phase accumulator |
| >+90° | 3 | Fast incrementing of phase accumulator |
| −10° . . . −45° | −1 | Slow decrementing of phase accumulator |
| −45° . . . −90° | −2 | Medium-fast decrementing of phase accumulator |
| <−90° | −3 | Fast decrementing of phase accumulator |

The arctangent elements 40 represent conversions from Cartesian into polar coordinates (e.g., only the angles). This may be performed in different ways (e.g., using the CORDIC algorithm or using tables). Without particularly high complexity, a conversion of input vectors up to 8 bit wide may be implemented using a table. A table may represent the mathematical function arctan(IM/RE) in the angle range of 0<Φ<pi (first quadrant). Using a decision tree, all 4 quadrants may be imaged on the first quadrant.

The VHDL code for such table may be as follows:

```
-----------------------------------------------------------------------
--Code for tcl_arctan
--generated 2012-08-02 12:19:04
-----------------------------------------------------------------------
library IEEE;
use IEEE.std_logic_1164.all;
use IEEE.std_logic_misc.all;
use IEEE.std_logic_unsigned.all;
use IEEE.std_logic_arith.all;
ENTITY tcl_arctan IS
```

```
    PORT(
      clk_H          : in std_logic;
      romAdr_H       : in std_logic_vector(13 downto 0);
      romDat_H       : out std_logic_vector(8 downto 0);
      enArcTanRamWr_H : in std_logic;
      ramAdr_H       : in std_logic_vector(13 downto 0);
      ramWrDat_H     : in std_logic_vector(8 downto 0);
      ramRdDat_H     : out std_logic_vector(8 downto 0)
      );
END tcl_arctan;
ARCHITECTURE tcl2vhd OF tcl_arctan IS
  --definition of the ram structure
    TYPE MemType IS array (0 to 16383) of std_logic_vector(8 downto 0); -- defines the ram matrix
    SIGNAL tclRamCells : MemType := (
        -- initialization values of ROM
        -- log
        "000000000", --Adress: 0 Imvalue: 0 ReValue: 0 arcTan: 0
        "000000000", --Adress: 1 Imvalue: 0 ReValue: 1 arcTan: 0.0
........
        "011111111", --Adress: 128 Imvalue: 1 ReValue: 0 arcTan: 1.5707963268
        "010000000", --Adress: 129 Imvalue: 1 ReValue: 1 arcTan: 0.785398163397
        "001001011", --Adress: 130 Imvalue: 1 ReValue: 2 arcTan: 0.463647609001
        "000110100", --Adress: 131 Imvalue: 1 ReValue: 3 arcTan: 0.321750554397
        "000100111", --Adress: 132 Imvalue: 1 ReValue: 4 arcTan: 0.244978663127
........
        "010000100", --Adress: 16376 Imvalue: 127 ReValue: 120 arcTan: 0.813730660815
        "010000011", --Adress: 16377 Imvalue: 127 ReValue: 121 arcTan: 0.809586993056
        "010000011", --Adress: 16378 Imvalue: 127 ReValue: 122 arcTan: 0.805475786411
        "010000010", --Adress: 16379 Imvalue: 127 ReValue: 123 arcTan: 0.801396798274
        "010000001", --Adress: 16380 Imvalue: 127 ReValue: 124 arcTan: 0.797349785538
        "010000001", --Adress: 16381 Imvalue: 127 ReValue: 125 arcTan: 0.793334504705
        "010000000", --Adress: 16382 Imvalue: 127 ReValue: 126 arcTan: 0.789350711984
        "010000000" --Adress: 16383 Imvalue: 127 ReValue: 127 arcTan: 0.785398163397
        );
  attribute ramstyle : string;
  attribute ramstyle of tclRamCells : signal is "M144K";
BEGIN -- tcl2vhd
romProcess : PROCESS (clk_H)
    BEGIN -- romProcess
      IF clk_H'EVENT and clk_H = '1' THEN
        IF enArcTanRamWr_H = '1' THEN
          tclRamCells(conv_integer(ramAdr_H)) <= ramWrDat_H;
        END IF;
        ramRdDat_H <= tclRamCells(conv_integer(ramAdr_H));
        romDat_H <= tclRamCells(conv_integer(romAdr_H));
      END IF;
    END PROCESS romProcess;
END tcl2vhd;
```

So as not to encode all 16 384 table values manually, the shown code is generated by a code generator. By way of example, this code generator may be a TCL program, as shown below:

```
#!/usr/local/bin/wish
set addressbits 14
set databits 9
set filename [lindex $argv 0]
wm withdraw .
proc insert_arctan {depth width} {
global log vhd
  set tcl_precision 64
  set pi [expr acos(-1)]
  set dataprecision [expr $width ] ;# also note sign bit!
  set maxInput $depth
  set maxDataValue [expr pow(2,$dataprecision + 1)]
  set lastAddress [expr $depth*$depth -1]
```

```
        for {set ImValue 0} {$ImValue < $maxInput} {incr ImValue} {
            for {set ReValue 0} {$ReValue < $maxInput} {incr ReValue} {
                # puts $log "generating values for address $addressvalue"
                set arcTanBin " "
                if {$ReValue == 0} {
                    if {$ImValue == 0} {
                        set arcTanVect 0
                    } else {
                        set arcTanVect [expr $pi/2]
                    }
                } else {
                set arcTanVect [expr atan(1.0*$ImValue/$ReValue)]
                }
                set arcTanVal $arcTanVect;
                set arcTanVect [expr $arcTanVect*2/$pi];# normalization to 1
                puts $log "$ImValue $ReValue $arcTanVect";
                #deal with sign bit of output
                if {$arcTanVect < 0} {
                   append arcTanBin "1"
                   set posSin 0
                   set negSin 1
                } else {
                   append arcTanBin "0"
                   set posSin 1
                   set negSin 0
                }
                set addressvalue [expr ($maxInput*$ImValue + $ReValue)]
                set arcTanVect [expr abs($arcTanVect)]
                for {set bitpos 1} {$bitpos < $dataprecision} {incr bitpos} {
                   set bitvalue [expr pow(2, -$bitpos )]
                   if {$arcTanVect >= $bitvalue} {
                      append arcTanBin $posSin
                      set arcTanVect [expr $arcTanVect - $bitvalue]
                   } else {
                      append arcTanBin $negSin
                   }
                }
                if {$addressvalue == $lastAddress} {
                   puts $vhd "        \"$arcTanBin\" --Adress: $addressvalue Imvalue: $ImValue
ReValue: $ReValue arcTan: $arcTanVal"
                } else {
                   puts $vhd "        \"$arcTanBin\", --Adress: $addressvalue Imvalue: $ImValue
ReValue: $ReValue arcTan: $arcTanVal"
                }
            }
        }
}
set filepath [file dirname $filename]
set logfile "${filepath}/vhdlgen.log"
if [catch {set log [open $logfile w]} msg ] {
   puts stderr "ERROR: Can't write to '$log': $msg"
   exit 1
}
puts $log "working in $filepath"
#set entity vhdfile
#set vhdfile "$entity.vhd"
regsub {\.tcl$} $filename ".vhd" vhdfile
regsub "$filepath/" $vhdfile "" tmp
set entity [lindex [split $tmp .] 0]
puts $log "entity name ist :$entity"
puts $log "vhd name ist :$vhdfile"
#set entity vhdfile
#set vhdfile "$entity.vhd"
if [catch {set vhd [open $vhdfile w]} msg ] {
   puts stderr "ERROR: Can't write to '$vhd': $msg"
   exit 1
}
puts $vhd "----------------------------------------------------------------------"
puts $vhd "--Code for $entity "
#puts $vhd "--generated [clock format [clock seconds] -format \"%Y-%m-%d
%H:%M:%S\"]"
puts $vhd "--generated [clock format [clock seconds] -format "%Y-%m-%d %H:%M:%S"]"
puts $vhd "----------------------------------------------------------------------"
puts $vhd "\nlibrary IEEE;"
puts $vhd "use IEEE.std_logic_1164.all;"
puts $vhd "use IEEE.std_logic_misc.all;"
puts $vhd "use IEEE.std_logic_unsigned.all;"
puts $vhd "use IEEE.std_logic_arith.all; \n\n"
puts $vhd "ENTITY $entity IS"
```

-continued

```
puts $vhd "   PORT("
puts $vhd "     clk_H       : in std_logic;"
puts $vhd "     romAdr_H    : in std_logic_vector([expr $addressbits - 1] downto 0);"
puts $vhd "     romDat_H    : out std_logic_vector([expr $databits   - 1] downto 0);"
puts $vhd "     enArcTanRamWr_H : in std_logic;"
puts $vhd "     ramAdr_H    : in std_logic vector([expr $addressbits - 1] downto 0);"
puts $vhd "     ramWrDat_H  : in std_logic_vector([expr $databits   - 1] downto 0);"
puts $vhd "     ramRdDat_H  : out std_logic_vector([expr $databits  - 1] downto 0)"
puts $vhd "     );"
puts $vhd "END $entity; \n\n"
puts $vhd "ARCHITECTURE tcl2vhd OF $entity IS\n"
puts $vhd "  --definition of the ram structure"
set romdepth [expr int(pow(2, $addressbits ))]
puts $log "depth of rom is $romdepth "
puts $vhd "TYPE MemType IS array (0 to [expr $romdepth- 1]) of std_logic_vector([expr
$databits   - 1] downto 0); -- defines the ram matrix"
puts $vhd "SIGNAL tclRamCells : MemType := ("
puts $vhd "        -- initialization values of ROM"
puts $vhd "        -- log"
set romdepth [expr int(pow(2, [expr $addressbits/2] ))];
insert_arctan $romdepth $databits
puts $vhd "        );\n\n"
puts $vhd ""
puts $vhd "   attribute ramstyle : string;"
puts $vhd "   attribute ramstyle of tclRamCells : signal is \"M144K\";"
puts $vhd ""
puts $vhd "BEGIN -- tcl2vhd\n"
puts $vhd "romProcess : PROCESS (clk_H)"
puts $vhd "    BEGIN -- romProcess"
puts $vhd "       IF clk_H'EVENT and clk_H = '1' THEN"
puts $vhd "          IF enArcTanRamWr_H = '1' THEN"
puts $vhd "             tclRamCells(conv_integer(ramAdr_H)) <= ramWrDat_H;"
puts $vhd "          END IF;"
puts $vhd "          ramRdDat_H <= tclRamCells(conv_integer(ramAdr_H));"
puts $vhd "          romDat_H <= tclRamCells(conv_integer(romAdr_H));"
puts $vhd "       END IF;"
puts $vhd "    END PROCESS romProcess;"
puts $vhd "END tcl2vhd;\n"
exit
```

The width of the input vectors influences the achievable signal dynamics. Since heating at low signal amplitude is very low, the required dynamic range is much smaller than for an RF closed-loop control. The transfer of the phase angle from the Cartesian closed-loop control into the phase closed-loop control need not be particularly precise, since the details of the phase error are still corrected by the Cartesian closed-loop control. There is, however, an increase of the phase closed-loop control range (e.g., for slowly changing phase errors, as occur, for example, in the case of the heating and cooling circulator).

Figure 9:
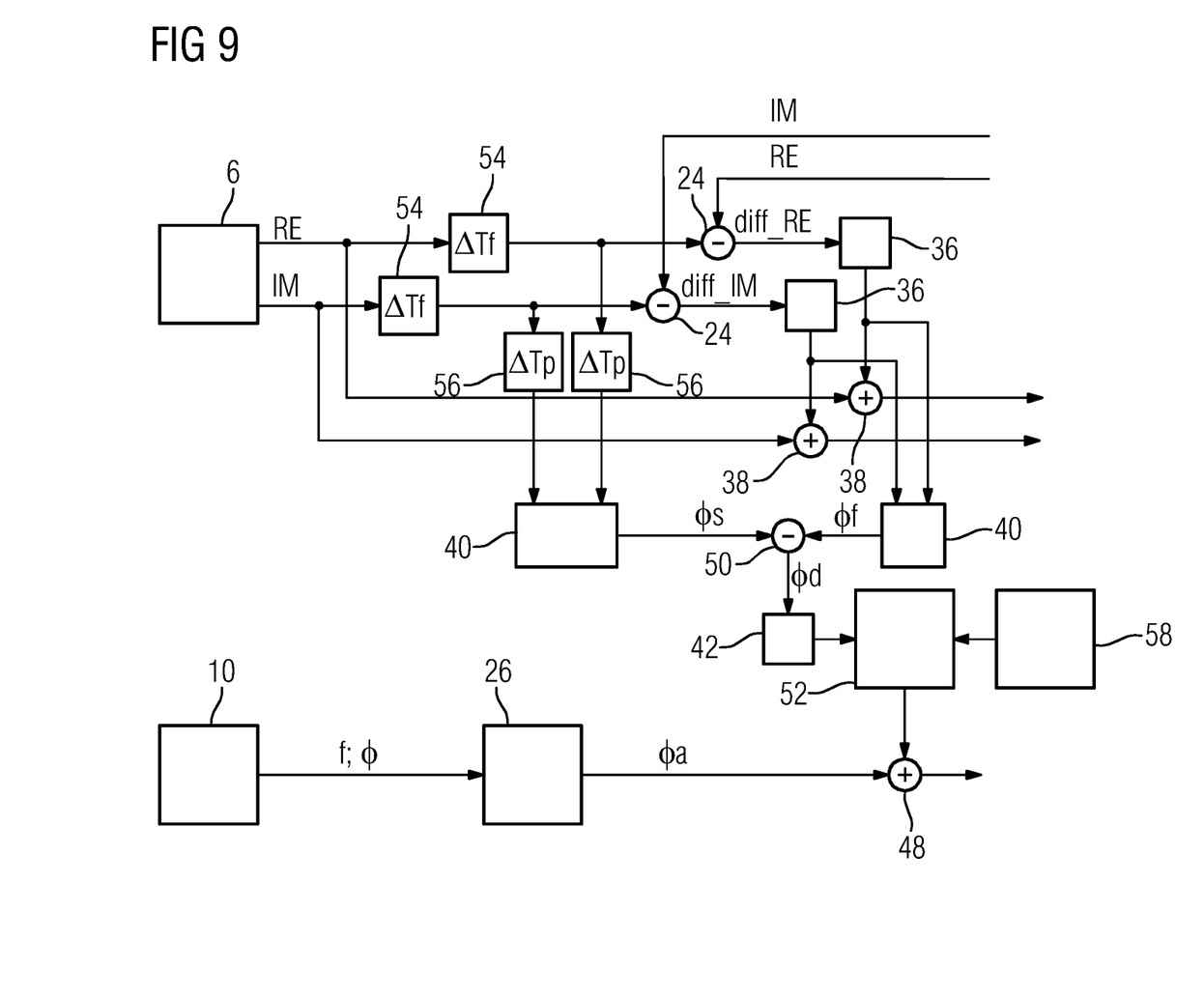

FIG. 9 shows a further refinement of FIG. 8 and, as an additional element compared to FIG. 8, shows a temperature model 58 of the circulator 16, which acts on the phase accumulator 52. This temperature model is always used during the pulse pauses, since the phase difference Φs-Φf is only valid during a radiofrequency pulse. Outside of the pulse, neither Φs nor Φf may be determined due to a lack of signal amplitude.

Between the radiofrequency pulses (or in measurement pauses), the circulator 16 cools and therefore, once again, changes the phase thereof. This phase change is modeled by the temperature model 58. As a result, the initial difference at the start of a radiofrequency pulse is improved. The parameters of the temperature model 58 depend on the design and the cooling of the circulator 16.

Figure 10:
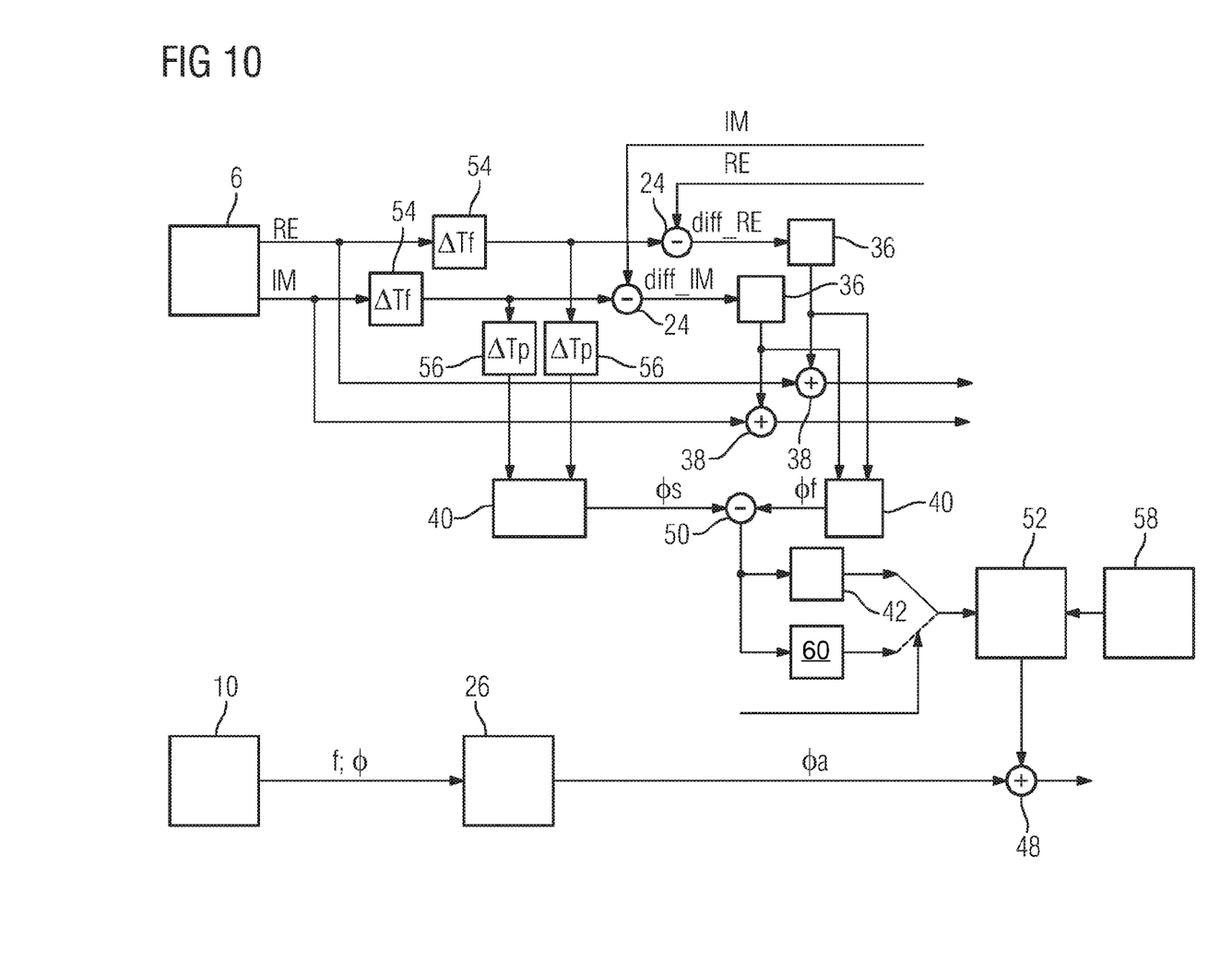

FIG. 10 depicts a further refinement of FIG. 9 and, as an additional element, shows a phase prediction block 60 that is arranged in a selectively actuatable bypass to the damping/gain element 42. This is because, at the end of the radiofrequency pulse, the phase error Φs-Φf remaining at the pulse end is present as residual error that could not be corrected previously during the pulse. If this value (possibly multiplied by a factor) is fed to the phase accumulator 52 at the end of a pulse, the phase accumulator 52 instantly jumps to the value caused by the circulator 16 as phase error. As a result, a quick correction may be carried out. Subsequently, in the pulse pause, the temperature model 58 is once again used. However, due to the pulse end, the phase jump is no longer effective in the radiofrequency pulse itself (e.g., the pulse is not interfered with by a phase jump).

Figure 11:
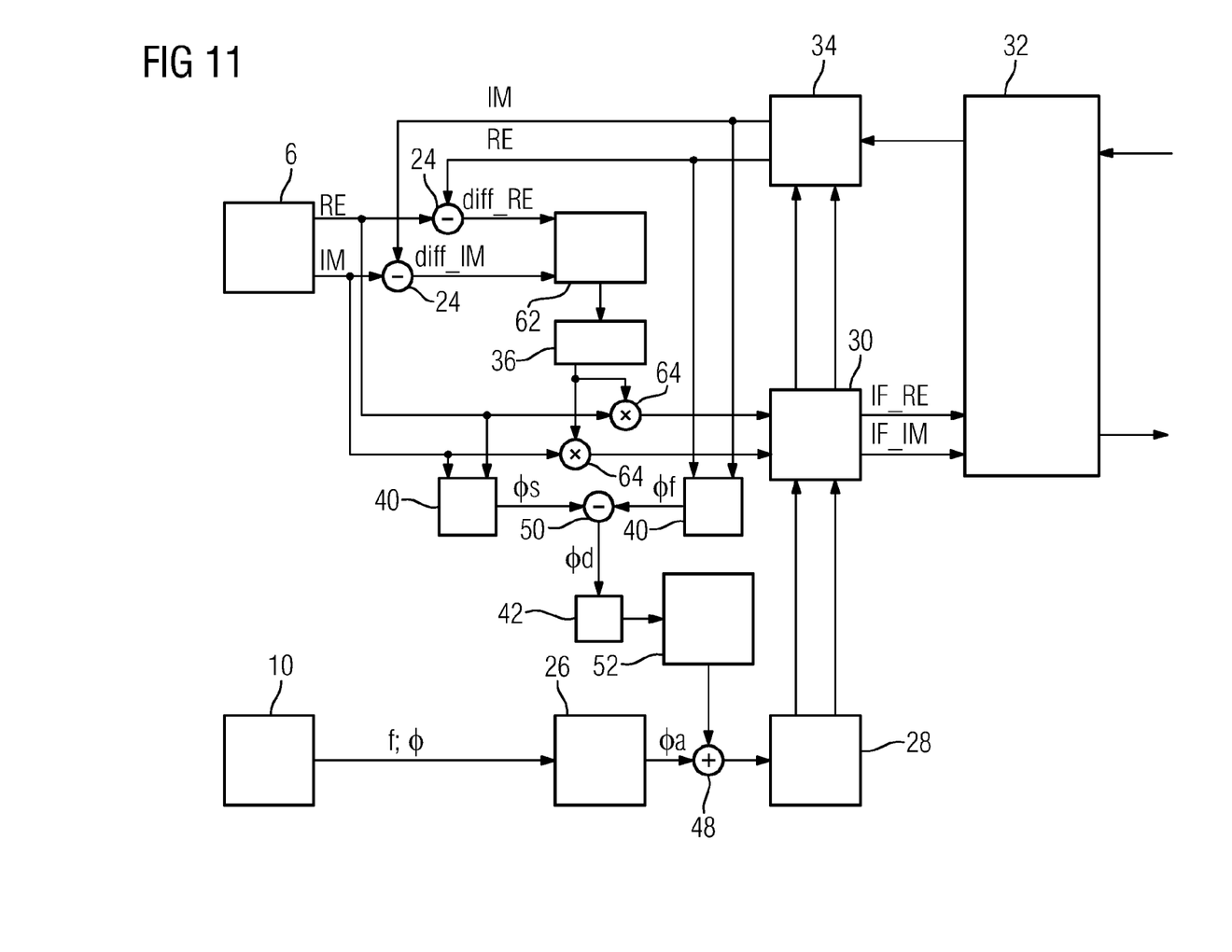

A further alternative solution leads to separate closed-loop control for amplitude and phase, similar to a polar coordinate closed-loop control. FIG. 11, which is explained based on differences to FIG. 6, shows the further alternative solution. The angle closed-loop control is brought about solely by the arctangent elements 40. The PID controllers 36 from FIG. 3 are replaced by a magnitude formation module 62 with a single PID controller 36 connected downstream thereof. The magnitude formation module establishes the real amplitude of the signal pair diff_RE and diff_IM. The addition elements 38 are replaced by scalar multiplication elements 64, which are fed from the PID controller 36. FIG. 11 also shows the additional phase accumulator 52.

The original Cartesian closed-loop control only still regulates the amplitude of the actuation signals RE and IM based on the difference vectors diff_RE and diff_IM. The control element is the scalar multiplication. The phase is corrected solely by the phase control loop to the extent already described. The advantage over combined Cartesian closed-loop control with an additional phase closed-loop control may lie in the closed-loop control property. The two phase control loops may work against one another under certain circumstances.

The magnitude formation in FIG. 11 may also still vary (e.g., take place at a different location). In one embodiment, it is not only the difference vectors that are subjected to magnitude formation, but it is already the actuation signals RE and IM and the actual signals feedback_IM and feedback_RE.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a signal for a transmission antenna in a magnetic resonance imaging system, the method comprising:
generating a real and imaginary part of a baseband signal;
generating a real and imaginary part of variations in frequency and in phase;
performing a complex multiplication of the baseband signal with the variations in frequency and in phase and a radiofrequency carrier signal for modulation;
modifying the modulated signal;
establishing an angle characteristic of a phase shift of the modified signal; and
correcting the modulation based on the established angle in a closed-loop control,
wherein the correcting comprises adding to an output signal of a phase accumulator that is used in the generation of a real and imaginary part of the variations in frequency and in phase.

2. The method of claim 1, wherein a difference between a phase angle of the demodulated modified signal and a phase angle of the baseband signal is used when establishing the characteristic angle.

3. The method of claim 2, wherein a phase angle of a manipulated variable of the closed-loop control is used when establishing the characteristic angle.

4. The method of claim 3, wherein a difference between a phase angle of the manipulated variable and a phase angle of the baseband signal is used when establishing the characteristic angle.

5. The method of claim 2, further comprising compensating for time retardation of elements of the closed-loop control.

6. The method of claim 5, wherein the phase accumulator is a first phase accumulator, and
wherein values are accumulated from the established angle using a second phase accumulator when correcting the modulation.

7. The method of claim 6, further comprising determining the values accumulated in the second phase accumulator based on a table with assignments between angle intervals and values.

8. The method of claim 2, wherein establishing the characteristic angle comprises determining the characteristic angle based on a table with assignments between real and imaginary part intervals and angles.

9. The method of claim 1, wherein a phase angle of a manipulated variable of the closed-loop control is used when establishing the characteristic angle.

10. The method of claim 9, wherein a difference between a phase angle of the manipulated variable and a phase angle of the baseband signal is used when establishing the characteristic angle.

11. The method of claim 1, further comprising compensating for time retardation of elements of the closed-loop control.

12. The method of claim 1, wherein the phase accumulator is a first phase accumulator, and
wherein values are accumulated from the established angle using a second phase accumulator when correcting the modulation.

13. The method of claim 12, further comprising determining the values accumulated in the second phase accumulator based on a table with assignments between angle intervals and values.

14. The method of claim 12, wherein modifying the modulated signal comprises modifying the modulated signal using a circulator, and wherein the method further comprises determining input values for the second phase accumulator based on a temperature of the circulator during a time period between two signal pulses of the signal.

15. The method of claim 14, wherein the residual established angle is fed to the second phase accumulator as an input value at the end of a signal pulse.

16. The method of claim 1, wherein establishing the characteristic angle comprises determining the characteristic angle based on a table with assignments between real and imaginary part intervals and angles.

17. A signal generation module for a magnetic resonance imaging system, the signal generation module being configured to generate signals, the signal generation module comprising:
a controller configured to:
generate a real and imaginary part of a baseband signal;
generate a real and imaginary part of variations in frequency and in phase;
perform a complex multiplication of the baseband signal with the variations in frequency and in phase and a radiofrequency carrier signal for modulation;
modify the modulated signal;
establish an angle characteristic of a phase shift of the modified signal; and
correct the modulation based on the established angle,
wherein the correction comprises addition to an output signal of a phase accumulator that is used in the generation of a real and imaginary part of the variations in frequency and in phase.

18. A magnetic resonance imaging system comprising:
a signal generation module configured to generate signals, the signal generation module comprising:
a controller configured to:
generate a real and imaginary part of a baseband signal;
generate a real and imaginary part of variations in frequency and in phase;

perform a complex multiplication of the baseband signal with the variations in frequency and in phase and a radiofrequency carrier signal for modulation;
modify the modulated signal;
establish an angle characteristic of a phase shift of the modified signal; and
correct the modulation based on the established angle,
wherein the correction comprises addition to an output signal of a phase accumulator that is used in the generation of a real and imaginary part of the variations in frequency and in phase.

* * * * *